(12) United States Patent
Kaval

(10) Patent No.: US 8,054,938 B2
(45) Date of Patent: *Nov. 8, 2011

(54) X-RAY IMAGING SYSTEM HAVING IMPROVED WEATHER RESISTANCE

(75) Inventor: Brian Kaval, Long Beach, CA (US)

(73) Assignee: Rapiscan Systems, Inc., Torrance, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 12/848,985

(22) Filed: Aug. 2, 2010

(65) Prior Publication Data

US 2011/0080999 A1    Apr. 7, 2011

Related U.S. Application Data

(63) Continuation of application No. 12/275,386, filed on Nov. 21, 2008, now Pat. No. 7,783,005, which is a continuation of application No. 11/404,386, filed on Apr. 14, 2006, now Pat. No. 7,471,764.

(60) Provisional application No. 60/671,900, filed on Apr. 15, 2005.

(51) Int. Cl.
*G01N 23/04* (2006.01)

(52) U.S. Cl. ........................................................ 378/57

(58) Field of Classification Search .................. 378/57, 378/203
See application file for complete search history.

(56) References Cited

U.S. PATENT DOCUMENTS

| | | | |
|---|---|---|---|
| 2,420,845 A | 5/1947 | Slack | |
| 2,885,069 A | 5/1959 | Bowen | |
| 4,481,403 A | 11/1984 | Del Monte | |
| 4,879,735 A | 11/1989 | Owens | |
| 4,884,289 A | 11/1989 | Glockmann et al. | |
| 5,260,983 A | 11/1993 | Ono et al. | |
| 5,970,113 A | 10/1999 | Ruth | |
| 6,134,299 A | 10/2000 | Artig | |
| 6,304,629 B1 | 10/2001 | Conway et al. | |
| 7,471,764 B2 * | 12/2008 | Kaval | 378/57 |
| 7,783,005 B2 * | 8/2010 | Kaval | 378/57 |
| 2004/0062346 A1 | 4/2004 | Fernandez | |
| 2005/0008120 A1 | 1/2005 | Ellenbogen | |
| 2005/0117700 A1 | 6/2005 | Peschmann | |
| 2006/0215811 A1 | 9/2006 | Modica et al. | |

* cited by examiner

*Primary Examiner* — Glen Kao

(74) *Attorney, Agent, or Firm* — Novel IP

(57) ABSTRACT

It is an object of the present invention to provide a radiation inspection system, such as an X-ray system, that can operate efficiently even in inclement weather conditions while being highly mobile. Thus the improved inspection system of the present invention is capable of operating in high temperature and corrosive environments and is designed to withstand moisture, dirt and/or dust from the articles of inspection as well.

11 Claims, 4 Drawing Sheets

X-RAY IMAGING SYSTEM HAVING IMPROVED WEATHER RESISTANCE

CROSS-REFERENCE TO RELATED APPLICATIONS

The present invention is a continuation of U.S. patent application Ser. No. 12/275,386 filed Nov. 21, 2008, which issued as U.S. Pat. No. 7,783,005, which is a continuation of U.S. patent application Ser. No. 11/404,386 filed Apr. 14, 2006, which issued as U.S. Pat. No. 7,471,764, which relies on, for priority, U.S. Provisional Patent Application No. 60/671,900, entitled "X-Ray System Having Improved Weather Resistance", filed on Apr. 15, 2005.

FIELD OF THE INVENTION

The present invention generally relates to the field of radiant energy imaging systems for detecting concealed objects, and more specifically to a detection system capable of operating in rugged, intense, and/or inclement weather environments. Specifically, the present invention is an X-ray inspection system having improved weather resistance. More specifically, the present invention is designed for use in outdoor venues and extreme temperatures.

BACKGROUND OF THE INVENTION

The inspection of baggage and/or other cargo at transit points such as airports and shipping ports has become almost universally mandatory. Luggage or cargo can be used for illegal transportation of contraband such as explosives, weapons, narcotics and dangerous chemicals. This warrants a rapid and accurate inspection system for determining the presence of concealed illegal materials.

X-ray scanning systems are the most widely used detection systems that provide for efficient inspection without the need for opening baggage. In conventional X-ray baggage systems, X-ray beams are directed through baggage as it is moved on a conveyor belt in a horizontal direction. The X-rays that have passed through the baggage are then processed for display on a video monitor to provide images of the contents of the baggage.

In general, conventional X-ray inspection systems work well within indoor environments, such as at airports. Conventional inspection systems, however, are also employed at ports, border crossings and customs checkpoints and/or sports venues, where space for housing and structures are not readily available. Thus, the ability of a system to operate outdoors becomes an important consideration.

Several components of conventional X-ray baggage systems are readily susceptible to damage when operating in inclement environments. For example, if a baggage inspection system is deployed in maritime environments such as a naval port, it must be able to endure the rigors of rain, sleet, salt spray and salt fog during operation.

These inclement weather elements could cause structural damage to conventional radiation shielding for the X-rays, thereby rendering the system hazardous to operate. Other parts of an X-ray inspection system that can be damaged due to moisture, humidity, dust and extreme temperatures, including the X-ray tube assembly and the collimator, which may alter the emission and scattering of X-rays, and the motors. In this case, not only the imaging quality of the system is adversely affected, but it also becomes electrically unsafe and unreliable.

Although most baggage inspection systems have a shielded housing for the X-ray tube, this alone is not sufficient to ensure unhindered functioning of the system in adverse weather conditions.

Attempts at improving the functioning of X-ray detection systems have largely focused on compensating for the effects of environmental factors on the system's detection capability. For example, U.S. Pat. No. 5,970,113 discloses a CT scanning system having a radiation source for directing radiation through a region and an array of detectors for receiving radiation from the region while scanning the region and for generating detector signals indicative of the received radiation, a method of compensating for electrical currents that are generated by the detectors independently of radiation received by the detectors, said method comprising: generating a calibration relationship for the array of detectors, said generating comprising: varying the temperature of the array of detectors, measuring the electrical currents generated by the detectors as the temperature of the detectors is varied, characterizing the variation in the electrical currents with temperature, using the variation in the electrical currents with temperature, generating a set of first detector offset signals to be applied to the detector signals generated while scanning the region; after generating the calibration relationship, sensing a first temperature of the array of detectors; measuring a first updated detector offset signal associated with the first temperature; scanning the region to generate a detector signal; sensing a second temperature of the array of detectors; using the second temperature, the calibration relationship, and the first updated detector offset signal, adjusting the first updated detector offset signal to generate an adjusted detector offset signal such that the adjusted detector offset signal is based on the first updated detector offset signal, the second temperature and the calibration relationship; and applying the adjusted detector offset signal to the detector signal.

This abovementioned prior art system, however, does not address the potential structural and internal damage that a detection system can incur when operated in harsh weather conditions. Conventional prior art baggage inspection systems are thus presently limited in their ability to withstand the effects of unfavorable and inclement operating environments.

What is therefore needed is a baggage inspection system that is capable of delivering optimum threat detection performance when operated in inclement weather.

Since dust or moisture on the baggage itself may also harm an inspection system, what is also needed is a baggage inspection system that is designed to both withstand inclement weather conditions and remain substantially unaffected by the type of baggage being scanned.

What is also needed is a system that is designed for mobility.

SUMMARY OF THE INVENTION

It is an object of the present invention to provide a radiation inspection system, such as an X-ray system, that can operate efficiently even in inclement weather conditions while being highly mobile. Thus the improved inspection system of the present invention is capable of operating in high temperature and corrosive environments and is designed to withstand moisture, dirt and/or dust from the articles of inspection as well. The X-ray system can be used to identify any type of item, including bombs, metals, knives, razors, explosives, drugs, narcotics, organic matter, such as plants, seeds, animals, insects, or meat products, or any other type of threat or undesirable item.

In accordance with an object of the present invention, one embodiment of the X-ray system comprises a conveyor belt system that loops along the external body of the x-ray system, instead of on the inside, as with conventional X-ray systems.

In another embodiment, the X-ray system of the present invention optionally comprises internal dehumidification devices and external vacuum-type cleaning devices to remove moisture and dust/dirt from the system.

In accordance with still another object of the present invention, the X-ray system comprises temperature regulating devices, such as internal cooling devices such as air conditioning and/or exhaust fans to remove heat generated during operation of the system as well as to cool the system from external high temperatures and heaters for warming the system in cold environments. The system preferably further comprises controls to either heat or cool the system.

It is also an object of the present invention to provide an inspection system that is capable of operating in outdoor weather conditions with minimal protective covering, limited, in one exemplary use, to an overhead canvas cover.

According to another aspect of the present invention, the inspection system is capable of at dual voltages (110/220 VAC) to comply with power requirements in virtually any geography.

In accordance with yet another object of the present invention the X-ray inspection system is portable and can be efficiently transported. A rugged, labeled, removable conveyor casing made up of either stainless steel or marine lumber material is provided for the system, which acts as a protective cover when the system is not in use and also when the system is to be transported from one place to another. Additional fixtures, such as fork tubes to facilitate movement using a standard forklift and sling-lift eyelet points to be hooked to the slings of a crane and be airlifted, are also provided that enable ease of transportation of the inspection system.

An embodiment of the present invention comprises software algorithms to process scan data to search the contents of an inspected object, such as baggage, for targeted material. The system differentiates low atomic number (low-Z), medium atomic number (medium-Z) and high atomic number (high-Z) materials by analyzing the size and dual energy transmissions of the object examined. The thus differentiated regions of the object are displayed to an operator in the form of a suitably color coded image.

A yet another embodiment of the present invention comprises software for training and testing the X-ray screening operators that randomly inserts fictional threat items such as guns, bombs, or knives into the X-ray image of the actual item undergoing screening.

In one embodiment, the X-ray imaging system for searching an object for concealed threats comprises an X-ray source encased in a first enclosure, a conveyor belt assembly arranged to loop around the external underside of said imaging device, an electronics system, such as a computer, detectors, data acquisition electronics, or power electronics, for controlling the X-ray source, processing data, or managing acquired images, and a conveyor belt. The electronic system is encased in at least one second enclosure. The system also includes a base frame physically integrated with at least one of said first or second enclosure wherein said base frame comprises a connector for transporting the system, and a display device for presenting an image of said object to an operator.

Optionally, the X-ray imaging system further comprises a plurality of cleaning elements for removing contaminants from said conveyor belt, wherein said cleaning element is at least one of a brush, blower, cleaning pad, or ionizer. The X-ray imaging system further comprises a plurality of heating elements for heating at least one of said X-ray source and electronics system. The X-ray imaging system further comprises a sensor for sensing a temperature and a controller wherein said controller controls the activation of said X-ray source or said electronics and wherein said controller activates said X-ray source or said electronics when said temperature sensed by said sensor exceeds a predetermined temperature. Optionally, the connector comprises at least one of a tube, beam, hook, indentation, or metal projection.

In one embodiment, the X-ray imaging system for searching an object for concealed threats comprises an X-ray source encased in a first enclosure, a conveyor belt assembly arranged to loop through the imaging device, an electronics system for controlling the X-ray source and conveyor belt, wherein said electronic system is encased in a plurality of separate enclosures, a base frame physically integrated with at least one of said first or plurality of separate enclosures wherein said base frame comprises a connector for transporting the system, and a display device for presenting an image of said object to an operator.

Optionally, the X-ray imaging system further comprises a plurality of cleaning elements for removing contaminants from said conveyor belt, wherein said cleaning element is at least one of a brush, blower, cleaning pad, or ionizer. The X-ray imaging system further comprises a plurality of heating elements for heating at least one of said X-ray source and electronics system. The X-ray imaging system further comprises a sensor for sensing a temperature and a controller wherein said controller controls the activation of said X-ray source or said electronics and wherein said controller activates said X-ray source or said electronics when said temperature sensed by said sensor exceeds a predetermined temperature. Optionally, the connector comprises at least one of a tube, beam, hook, indentation, or metal projection. Optionally, the X-ray imaging system further comprises removable covers enclosing at least a portion of said conveyor belt.

The aforementioned and other embodiments of the present shall be described in greater depth in the drawings and detailed description provided below.

BRIEF DESCRIPTION OF THE DRAWINGS

These and other features and advantages of the present invention will be appreciated, as they become better understood by reference to the following detailed description when considered in connection with the accompanying drawings, wherein.

DETAILED DESCRIPTION OF THE INVENTION

The methods and systems described herein are directed towards finding, locating, and confirming threat items and substances. The present invention is specifically directed towards an improved inspection system for screening objects at security locations. The system of the present invention is capable of functioning in inclement weather and rugged operating environments while retaining the efficiency of the screening process.

More specifically, the present invention is directed towards an x-ray system for use in adverse, outdoor weather conditions, with temperatures ranging between 0 to 110° F. (−17 to +43° C.) and is intended to be operated with minimal protective covering, such as, in one exemplary use, to an overhead canvas cover. The cover is used to provide protection from direct sunlight to the operator's eyes, and to provide an anti-glare environment to control unnecessary fatigue.

The system of the present invention further comprises a conveyor belt that runs along the outside of the x-ray system, compared with conventional X-ray systems, in which the conveyor system runs through the inside of the system. This configuration helps keep moisture, dirt, dust, and other foreign elements from the bags out of the system and enables better sealing and protection of the electronics. In another embodiment, the conveyor belt entirely runs through the x-ray system with cleaning elements positioned inside the x-ray system to keep the system substantially clean.

To facilitate rapid deployment, the system is equipped with dual voltage capability (110/220 VAC) to comply with power requirements in virtually any geographical environment.

Although the embodiments are described in the context of a baggage inspection system, it should be evident to persons of ordinary skill in the art that items other than luggage such as other packages, mail, and cargo-containers, or even processed food stuffs, can also be analyzed and screened or graded and that the descriptions are exemplary and are not restrictive of the invention.

Although one preferred embodiment of the present invention is described with reference to X-ray scanning, one of ordinary skill in the art would appreciate that object screening may be performed using any available radiation imaging technique such as, but not limited to X-ray scattering, infrared imaging, milliwave imaging, RF imaging, radar imaging, holographic imaging, CT imaging, and MRI. Any imaging system that has the potential for displaying object detail may be employed.

Reference will now be made in detail to specific embodiments of the invention. While the invention will be described in conjunction with specific embodiments, it is not intended to limit the invention to one embodiment.

Figure 1:
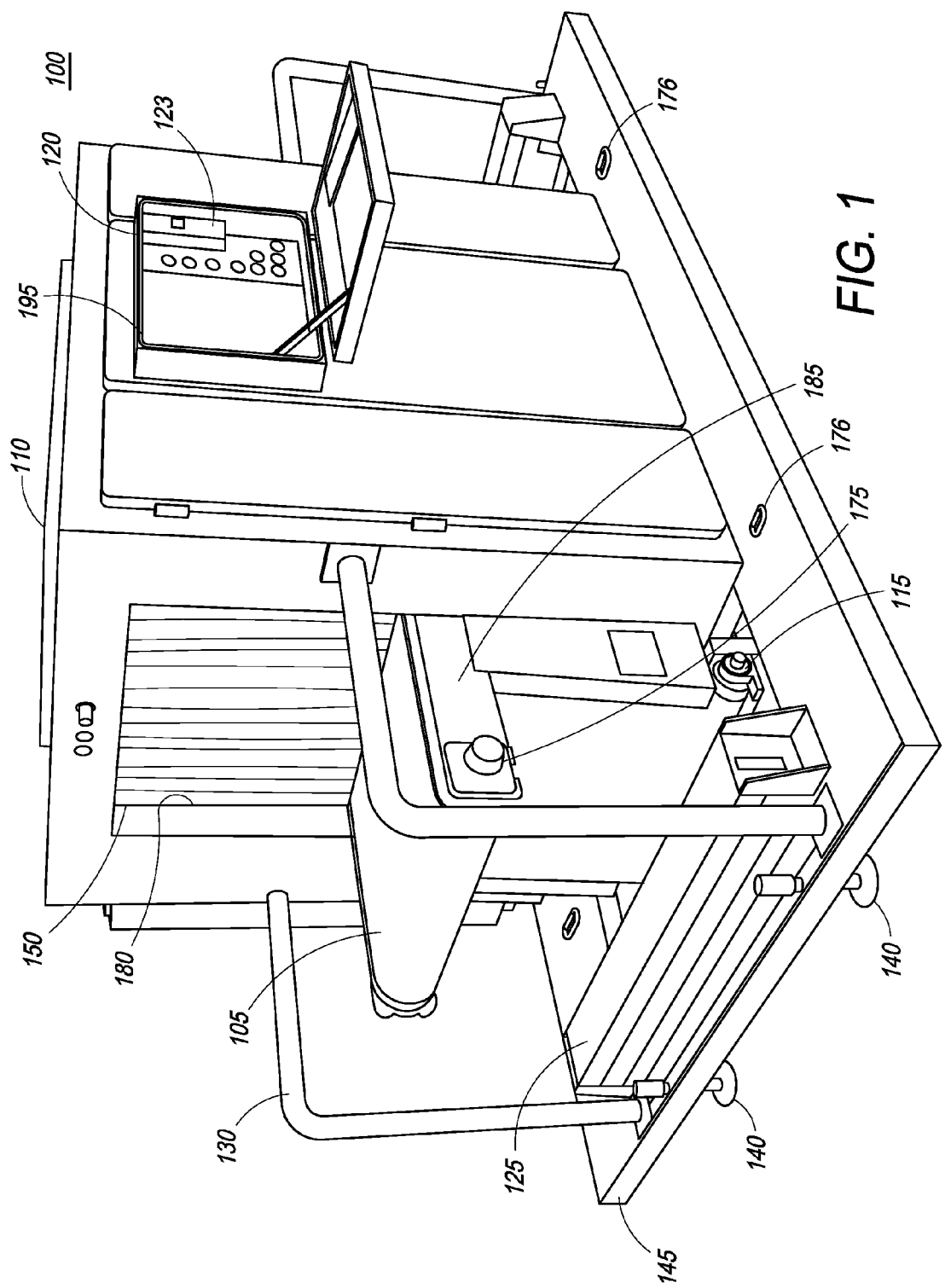
FIG. 1 illustrates the basic structural design of the X-ray imaging system having improved weather resistance of the present invention.

FIG. 1 illustrates the basic structural design of the X-ray imaging system having improved weather resistance of the present invention. Referring to FIG. 1, X-ray baggage scanning system 100 comprises an enclosure 110 mounted on a base frame 145. To provide structural reinforcement and a means by which the X-ray imaging system can be safely and reliably moved, the X-ray imaging system further comprises beams 130 that connect the enclosure 110 to the base frame 145 and base beams 125 that extend a substantial portion of the length of the base frame 145. In one embodiment, the base beams 125 are scissor lifts that can be deployed to lower wheels, thereby enabling the system to be rolled. Preferably, if the system is to remain stationary, the wheels are retracted and jacking feet 140 are used to stabilize the system.

It should be appreciated by one of ordinary skill in the art that the base frame 145 can be solid or comprised of a plurality of connected panels. The beams 130 can be L-shaped as depicted in FIG. 1, straight, or any other configuration that provides sufficient structural support. It should be appreciated that the beams 130 are positioned to protect the belt and conveyor belt from being damaged which could occur, for example, if the system is rolled against a wall or protusion.

Further the base frame 145 comprises connection points 176 that can be used to connect to hooks, cabling, or other towing mechanisms for airlifting, pushing, pulling, or otherwise moving the system 100. The connection points can comprise a hook, indentation, such as a slot cut, hole, or key slot, or any type of projection of any material type, such as metal or plastic.

The enclosure 110, base frame 145, beams 130, and base beams 125 are preferably constructed using regular steel painted with marine grade paint or stainless steel, enabling the system to function in both outdoor as well as industrial environments. In such conditions, apart from the weather elements, the system may also be exposed to caustic chemicals. This is particularly the case with industrial environments such as the packaged food or meat industry, where the X-ray scanning system may be employed for checking food materials for contaminants. In addition, any electronics, instrumentation, and display panels, such as control panel 123, are encased in regular steel painted with marine grade paint or non-corrosive stainless steel paneling 120.

The X-ray baggage scanning system 100 comprises an inspection entrance 150 covered by a lead curtain 180. Objects to be inspected are placed on an extended roller surface 185 covered by a conveyor belt 105 which extends below the extended roller surface 185, downward 175, and over base roller 115. During operation, the conveyor belt 105 moves forward, through entrance 150 and lead curtain 180, and loops around extended roller surface [not shown], downward, and over a base roller [not shown]. The conveyor belt 105 moves over the base roller 115, upward, and over extended roller surface 185. It should be appreciated that the conveyor belt 105 can move in either direction.

The conveyor apparatus of the scanning system is in constant and continual contact with different types of items under inspection, including baggage. Not all items of inspection, however, are clean, dry and/or ready to be placed into an X-ray system. This is especially true if the inspection system is operated outdoor, and in particular with inclement weather, or in rugged industrial environments. Thus, depending upon the location of inspection, the objects of inspection may be dusty, moist, or even contaminated with other environmental factors.

In one embodiment the enclosure 110, toward the base of the structure, comprises a plurality of cleaning elements [not shown] that remove water, dirt, chemicals, and other foreign substances from the conveyor belt 105 surface in order to prevent the introduction of any substances which could damage the internal detector systems and radiation sources. The cleaning elements can comprise any one of brushes, pads, blowers, dryers, ionizers, or other devices that can substantially remove foreign substances from the conveyor belt surface.

Figure 3:
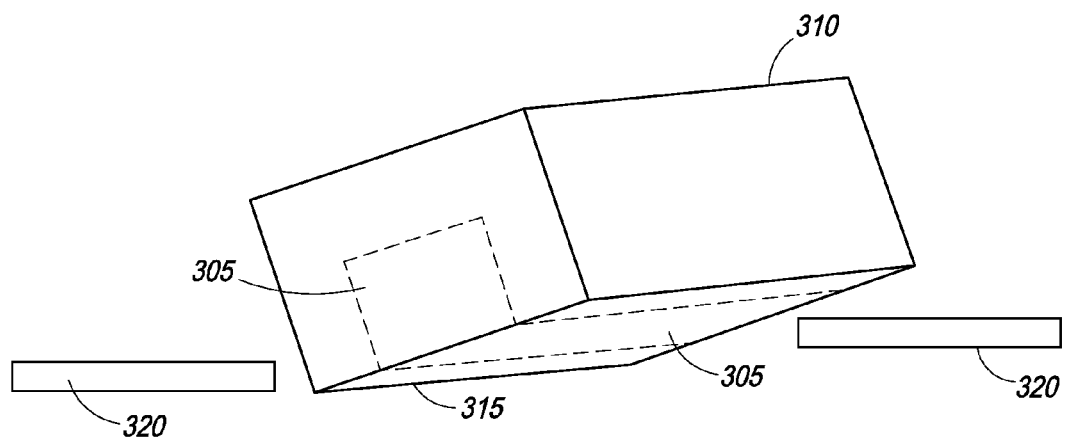
FIG. 3 is schematic of the X-ray scanning system of the present invention illustrating the external underside of the scanning system.

FIG. 3 is a block diagram of the X-ray scanning system of the present invention, in particular, illustrating the external underside of the scanning system. FIG. 3 depicts X-ray scanning system 310 further illustrating the external underside 315 of X-ray unit 310. The conveyor belt 305 is depicted with a dotted outline. If baggage placed on the conveyor 305 is wet or dirty, the external face of the belt runs on the outside of the machine to allow it to drip off, and the conveyor belt 305 is substantially dry when it comes in contact with and loops back through the X-ray unit 310. The system may further comprise at least one vacuum or suction-type cleaning device 320, which are well-known to persons of ordinary skill in the art. Vacuum or suction-type cleaning devices 320 may thus be employed to draw out the dust on the conveyor belt 305 as it runs along the outside 315 of the enclosure 310.

One of ordinary skill in the art would appreciate that the enclosure 110 encompasses a plurality of detectors and radiation sources [not shown] that expose objects to be inspected to radiation and measures the resulting output. Such detector/radiation source combinations can include X-ray transmission and/or scatter detection systems.

Figure 2:
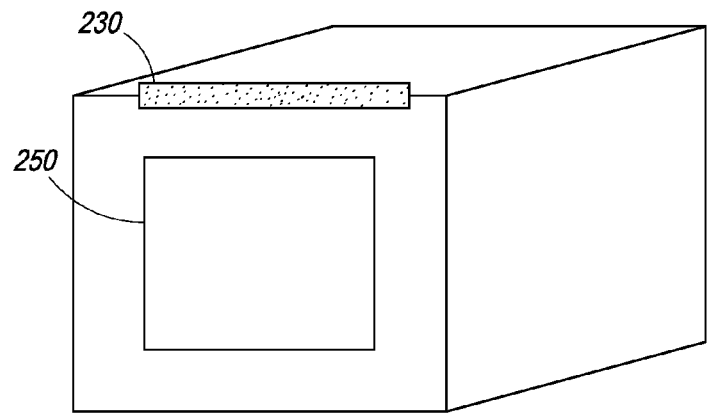
FIG. 2 is a schematic diagram illustrating the placement of an environmental control system.

Referring to FIG. 2, the system contains an environmental control system 230 that ensures the electronic components remain dry and cool. In one embodiment, the environmental control system 230 comprises an internal high-reliability, interlocked dehumidifier to ensure that the electronic components remain dry and cool. In another embodiment, the environmental control system 230 comprises an internal cooling device that compensates for the external heat as well as for the heat generated during operation. Optionally, a temperature control device or air conditioning device, known to persons of ordinary skill in the art, is interlocked internally within the system of the present invention. The air conditioning device has sufficient cooling capacity depending upon the load/size of the inspection system and the external temperatures. In another embodiment exhaust fans are provided on the chassis of the inspection system that constantly withdraw heat generated in the internal components of the machine.

In another embodiment, heaters are provided and configured to keep varied portions of the system warm. Separate heaters are preferably provided for the X-ray source and electronics. Also preferably, the electronics and X-ray source do not turn on until a threshold temperature is reached. Therefore, the system further comprises a sensor for measuring the temperature and a controller for permitting the X-ray source and/or electronics to turn on, upon reaching a predetermined threshold temperature, as determined by the sensor, and receiving an activation signal from an operator.

Figure 4:
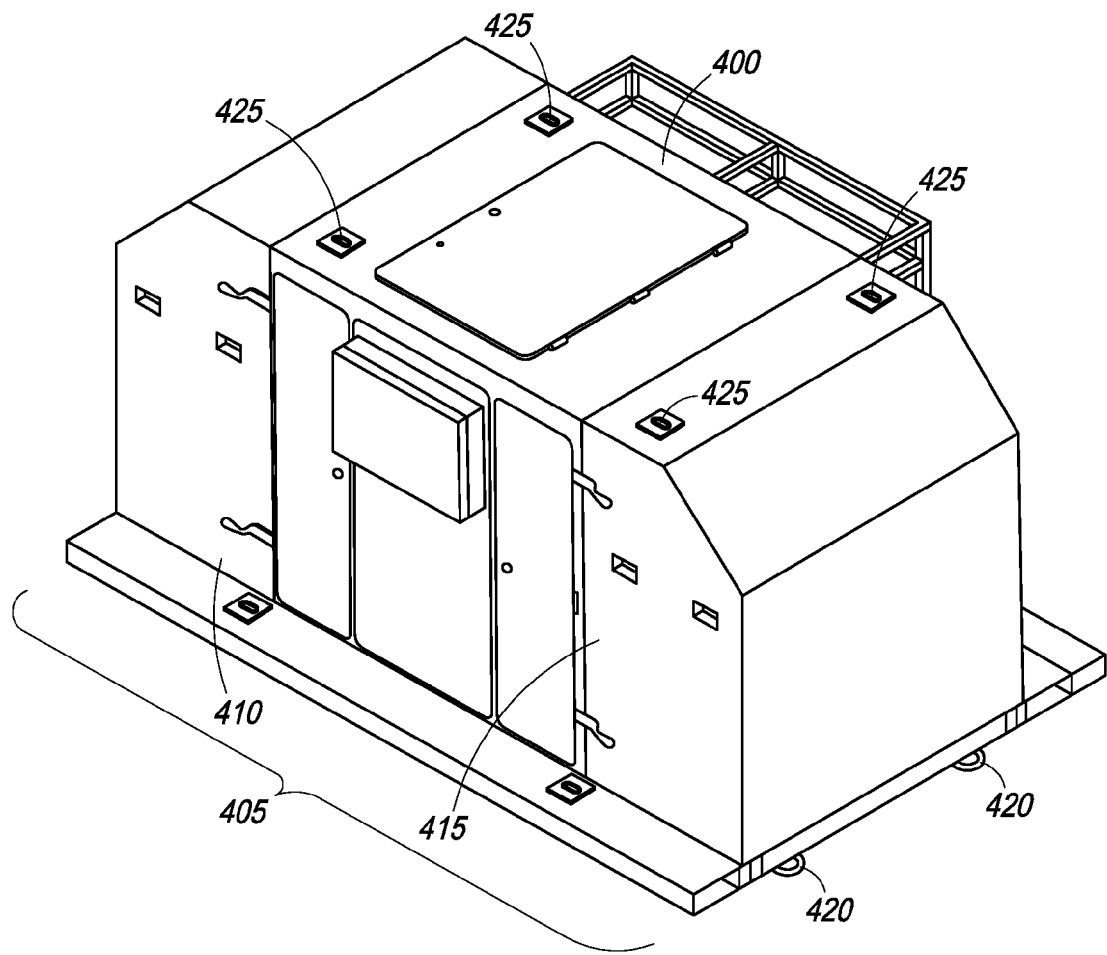
FIG. 4 depicts another embodiment of the system of present invention.

In another embodiment, a rugged, labeled, removable casing made up of either stainless steel or regular steel painted with marine grade paint is provided for the system, which acts as a protective cover for the conveyor belt when the system is not in use and also when the system is to be transported from one place to another. FIG. 4 depicts the system 400 of the present invention with the protective casing 405. The protective casing 405 is especially useful during transportation of the system 400, as it prevents damage to the belts and tunnels of the units at the time of loading and unloading. In order to enhance the ease of transportation, the protective case 405 is designed such that it fits over the system 400 in two pieces, 410 and 415, in a manner that exposes a set of fork tubes 420, which are provided to facilitate movement using a standard forklift. In addition or alternatively, threaded, sling-lift eyelet points 425 are provided at the four corners of the casing 405, which enable the system 400 to be hooked to the slings of a crane and be airlifted. Preferably, however, connection points on the base frame are used to connect to hooks, cabling, or other towing mechanisms for airlifting, pushing, pulling, or otherwise moving the system. The connection points can comprise a hook, indentation, such as a slot cut, hole, or key slot, or any type of projection of any material type, such as metal or plastic. It should be appreciated that the present configuration is designed to protect the system from damage during transport while still enabling a fast setup of the system. This is achieved by providing casing covers for only the conveyor belt and not encompassing the entire system in a separate casing or crate during transport.

In one embodiment, the system depicted in FIG. 4 has a length of 90 to 120 inches, a height of 40 to 70 inches, and a width of 50 to 80 inches. The conveyor belt, which is covered by case 405, progresses through a tunnel of dimensions 29.53 inches to 21.65 inches at a rate of 30 to 50 ft/min. The conveyor is preferably capable of handling a load of 350 to 450 lbs. The approximate weight of the system is 4000 to 4500 lbs. For power, the system has dual voltage capability (110/220 VAC). The X-ray image performance has a minimum penetration of 25 mm and a standard penetration of 29 mm. The X-ray generator is cooled using a sealed oil bath with forced air and has an anode voltage rated at 160 KV and operating at 140 KV. The X-ray generator is oriented vertically upward, toward the top-level conveyor belt. It can be stored in temperatures ranging from negative 20 degrees C. to 50 degrees C., operated in temperatures ranging from negative 17 degrees C. to 43 degrees C., and stored or operated in relative humidity ranging from 0 to 100% condensing. The system preferably complies with US military salt spray requirements embodied in MIL-STD-810F, which is incorporated herein by reference.

During operation, an item under inspection is first carried along the conveyor belt 105, which, in turn, carries the item into the aperture defining the entrance 150 to scanning system 100 and through the lead curtain 180. As the item under inspection passes through the X-scanning system 100, an image of the contents of the item is displayed upon display screen 185. The generation of X-ray transmission or scatter images is known to persons of ordinary skill in the art and will not be repeated herein.

Apart from robustness, the present invention focuses on ease of operation while maintaining high levels of performance. A preferred embodiment of the system uses preset software algorithms, as known to persons of ordinary skill in the art, to search baggage contents for targeted material. During the analysis process the size and atomic number of the material(s) are examined, and low atomic number (low-Z), medium atomic number (medium-Z) and high atomic number (high-Z) material are differentiated. This differentiation is presented to the screening operator in an easy visual manner, such as by highlighting materials with different atomic numbers in different colors. The present application incorporates the X-ray analytical systems disclosed in U.S. patent application Ser. No. 10/910,250, entitled "Automatic Alarm Resolution for Explosive Detection System", by reference.

For example, the system is capable of distinguishing between materials according to their inherent characteristics (densities) and then classifies for the operator by color. For example, but not limited to such color scheme, orange is used for low atomic density, green for medium atomic density and blue for high atomic density material. Most explosives are in the low atomic density and thus will be displayed in orange. Other low density materials such as plastics, clothing, and paper will also be shown in orange. Medium density materials such as aluminum will be displayed in green, while very dense materials like metals will be shown in blue. In situations where X-rays cannot penetrate an object due to a combination of thickness and/or density, the image color will be black. This is the case for items such as lead glass vases, and thick metals. Obviously because X-rays are not getting through a black colored item, the bag needs to be opened and inspected, as there is a concealment zone in there.

Figure 5:
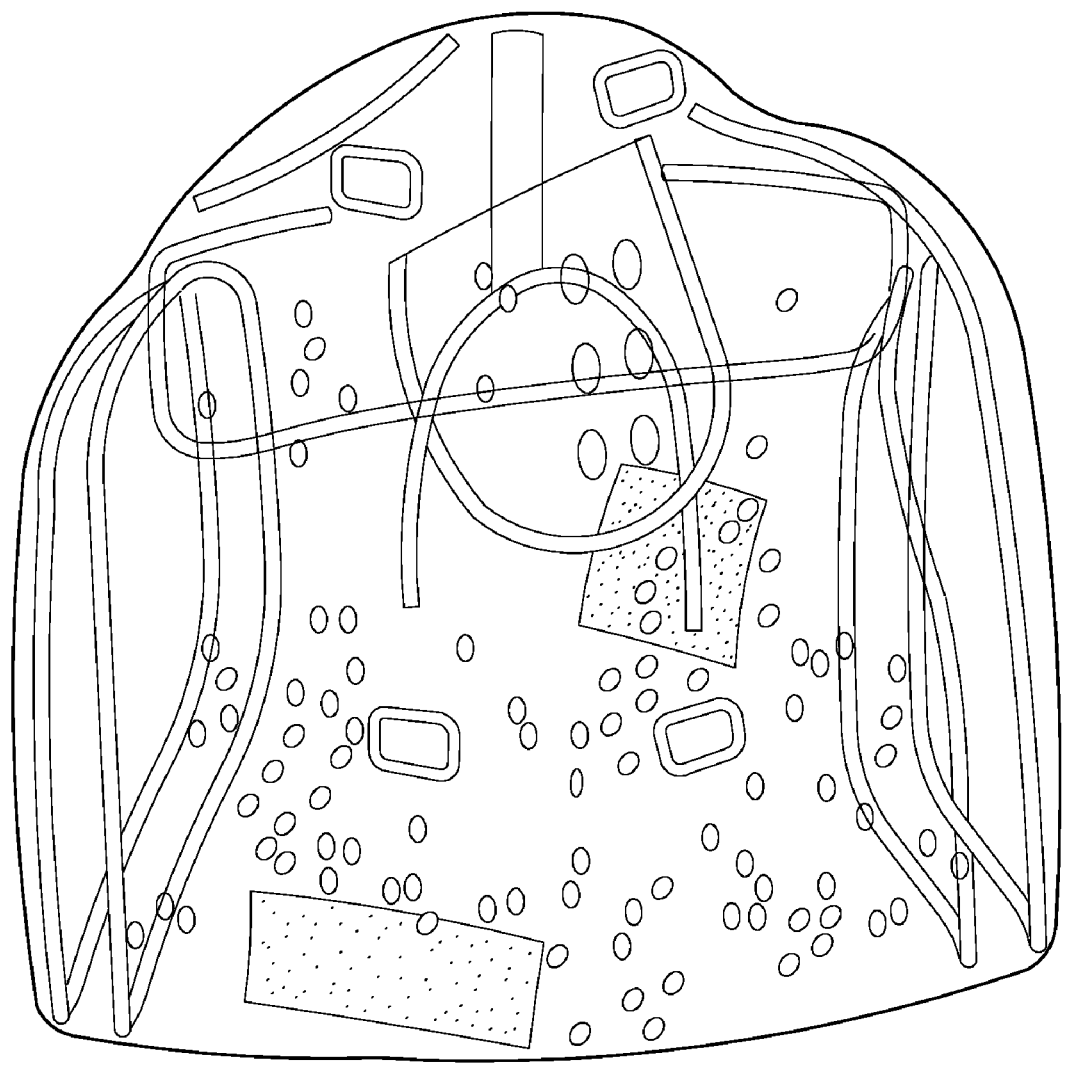
FIG. 5 illustrates an exemplary X-ray scan image with embedded fictional threat items.

Another embodiment of the system also provides a reliable and sophisticated method for the training and testing of X-ray screening personnel. This involves using a software package that randomly inserts fictional threat items such as guns, bombs, or knives into the X-ray image of the actual item undergoing screening. An example of such an image with illusory threat objects is illustrated in FIG. 5. This process enhances the alertness and threat recognition skills of the operators, and also provides performance data to supervisors for monitoring the operators' response. This application is detailed in U.S. application Ser. No. 11/343,747, assigned to the applicant of the present invention, and is incorporated herein by reference. In another embodiment, the present invention outputs data, through a wireless or wired network, to a central station that permits a single user to supervise the performance of multiple X-ray checkpoints.

In another embodiment, the present invention comprises a control panel that is protected from water and other contaminants using a clear plastic or glass cover. Furthermore, the control panel can include environmental indicators, such as temperature, humidity, and wind speed. Alternatively, such indicators can be located anywhere else on the system.

The above examples are merely illustrative of the many applications of the system of present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

The invention claimed is:

1. An X-ray imaging system for scanning an object comprising:
    an X-ray source encased in a first enclosure, wherein said first enclosure has a first side and a second side;
    a conveyor belt assembly having a first end and a second end;
    an electronics system for controlling the X-ray source and conveyor belt, wherein said electronics system is encased in at least one second enclosure;
    a base frame physically integrated with at least one of said first or second enclosures;
    a protective casing that is configured to fully cover the first end of said conveyor belt assembly and physically attach to said base frame; and
    a display device for presenting an image of said object to an operator.

2. The X-ray imaging system of claim 1 further comprising a plurality of cleaning elements for removing contaminants from said conveyor belt.

3. The X-ray imaging system of claim 2 wherein said cleaning elements comprise at least one of a brush, blower, cleaning pad, or ionizer.

4. The X-ray imaging system of claim 1 further comprising a plurality of heating elements for heating at least one of said X-ray source and electronics system.

5. The X-ray imaging system of claim 1 further comprising a sensor for sensing a temperature and a controller wherein said controller controls the activation of said X-ray source or said electronics system.

6. The X-ray imaging system of claim 5 wherein said controller activates said X-ray source or said electronics system when said temperature sensed by said sensor exceeds a predetermined temperature.

7. The X-ray imaging system of claim 1 wherein said base frame comprises a connector for transporting the system.

8. The X-ray imaging system of claim 7 wherein said connector comprises at least one of a tube, beam, hook, indentation, or metal projection.

9. The X-ray imaging system of claim 1 wherein said protective casing comprises a first portion that is configured to fully cover the first end of said conveyor belt assembly and physically attach to said base frame and a section portion that is configured to fully cover the second end of said conveyor belt assembly and physically attach to said base frame.

10. The X-ray imaging system of claim 1 wherein said first enclosure has an underside with an external surface and wherein said conveyor belt assembly is arranged to loop around the external surface of the underside of said first enclosure.

11. The X-ray imaging system of claim 1 and wherein the first end extends beyond the first side of the first enclosure and the second end extends beyond the second side of the first enclosure.

\* \* \* \* \*